United States Patent [19]
Jina

[11] Patent Number: 6,046,051
[45] Date of Patent: Apr. 4, 2000

[54] METHOD AND DEVICE FOR MEASURING BLOOD COAGULATION OR LYSIS BY VISCOSITY CHANGES

[75] Inventor: Arvind N. Jina, Milpitas, Calif.

[73] Assignee: Hemosense, Inc., San Jose, Calif.

[21] Appl. No.: 08/884,027

[22] Filed: Jun. 27, 1997

[51] Int. Cl.$^7$ .................................................. G01N 33/86
[52] U.S. Cl. .............................. 436/69; 422/56; 422/73; 422/82.01; 422/82.02; 73/54.01; 73/54.02; 600/369
[58] Field of Search .............................. 436/69; 422/56, 422/58, 82.01, 82.02, 73; 73/54.01, 54.02; 600/369

[56] References Cited

U.S. PATENT DOCUMENTS

| Re. 30,007 | 5/1979 | Steuer et al. | 324/442 |
|---|---|---|---|
| 3,674,012 | 7/1972 | Sage | 600/369 |
| 3,911,728 | 10/1975 | Fixot | 73/54.04 |

(List continued on next page.)

FOREIGN PATENT DOCUMENTS

| WO93/09439 | 5/1993 | WIPO . |
|---|---|---|
| WO95/06868 | 3/1995 | WIPO . |

OTHER PUBLICATIONS

McIntire, et al., Electrochemistry in Ordered Systems, Electrochemical and Spectroscopic Examination of the Interactions between Nitrobeneze and Anionic, Cationic, and Nonionic Micellas, Center for Catalytic Science and Technology and Brown Chemical Laboratory, The University of Delaware, Aug. 13, 1991.

Zweig, et al., Membrane–Based, Dry Reagent Prothrombin Time Tests, Biomedical Instrumentation & Technology, May/Jun. 1996, pp. 245–256.

Tripodi, et al., Clinical Evaluation of a Fully Automated Chromogenic Method for Prothrombin Time Compared with a Conventional Coagulation Method, Clinical Chemistry, vol. 30, No. 8, 1984, pp. 1392–1395.

Okada et al., An Electrical Method to Determine Hematocrits, IRE Transactions on Medical Electronics, pp. 188–192, Date Unknown.

(List continued on next page.)

*Primary Examiner*—Maureen M. Wallenhorst
*Attorney, Agent, or Firm*—Timothy H. Gens; Trial & Technology Law Group

[57] ABSTRACT

The present invention provides a single-use electronic device and test card for use therein which performs a coagulation or lysis assay of a blood sample. The device includes a housing having an exterior surface and defining an interior area and means for receiving the sample through the housing into the interior space. A non-porous substrate is positioned within the interior space for receiving the sample thereon. A reagent accelerates the coagulation of the sample and is positioned on the substrate and in contact with the sample. Optionally, an electroactive species may also be reacted with the sample. The device also includes means for measuring the viscosity of the sample and generating an electrical signal which correlates to a curve of the coagulation/lysis assay. Processing means positioned within the interior space is connected to the measuring means for receiving and converting the electrical signal into a digital output corresponding to the coagulation/lysis assay using assay calibration information stored therein. Display means visually displays the digital output external to the housing and is connected to the processing means. A method of determining the coagulation or lysis of a sample provides for accelerating the coagulation of the sample by chemically reacting the sample with at least one reagent on the substrate to produce a detectable change in the viscosity of the sample which correlates with the state of coagulation or lysis of the sample and measuring the viscosity of the sample and generating an electrical signal which correlates to a curve of the coagulation/lysis assay.

17 Claims, 6 Drawing Sheets

U.S. PATENT DOCUMENTS

| | | | |
|---|---|---|---|
| 4,303,887 | 12/1981 | Hill et al. | 324/441 |
| 4,947,678 | 8/1990 | Hori et al. | 73/54.42 |
| 5,059,525 | 10/1991 | Bartl et al. | 435/13 |
| 5,112,455 | 5/1992 | Cozzette et al. | 205/778 |
| 5,200,051 | 4/1993 | Cozzette et al. | 204/403 |
| 5,344,754 | 9/1994 | Zweig | 435/4 |
| 5,350,676 | 9/1994 | Oberhardt et al. | 435/13 |
| 5,385,846 | 1/1995 | Kuhn et al. | 436/70 |
| 5,418,141 | 5/1995 | Zweig et al. | 435/13 |
| 5,418,143 | 5/1995 | Zweig | 435/13 |
| 5,447,440 | 9/1995 | Davis et al. | 435/6 |
| 5,452,601 | 9/1995 | Hori et al. | 73/54.42 |
| 5,488,816 | 2/1996 | Grage, Jr. et al. | 53/471 |
| 5,491,408 | 2/1996 | Rousseau | 324/71.1 |
| 5,526,120 | 6/1996 | Jina et al. | 356/446 |
| 5,580,794 | 12/1996 | Allen | 436/169 |
| 5,601,995 | 2/1997 | Exner | 435/13 |
| 5,628,961 | 5/1997 | Davis et al. | 422/63 |
| 5,629,209 | 5/1997 | Braun, Sr. et al. | 436/69 |

OTHER PUBLICATIONS

Washburn, The Measurement of Electrolytic Conductivity. I. The Theory of the Design of Conductivity Cells, The Measurement of Eletrolytic Conductivity, pp. 2431–2403, Date Unknown.

Rosenthal, et al., Measurement of the Electric Resistance of Human Blood; Use in Coagulation Studies and Cell Volume Determinations, Electric Resistance of Human Blood, pp. 1110–1122, Date Unknown.

McKay, et al., Microemulsion Structure and Its Effect on Electrochemical Reactions, Analytical Chemistry, vol. 52., No. 10, May 15, 1990, pp. 1084–1090.

Dayalan, et al., Micelle and Microemulsion Diffusion Coefficients, Dept. of Chemical Engineering, Case Western Reserve University, Cleveland, Ohio, Imaging Research Laboratories, Eastman Kodak Co., Rochester, N.Y., pp. 119–135, Date Unknown.

Hirsch, et al., The Electrical Conductivity of Blood, Blood, 1950, pp. 1017–1035.

Bard, et al., Electrochemical Methods Fundamentals and Applications, John Wiley and Sons, 1980, pp. 136–141, 213–215, 227–231, 249–277, and 703–718.

TAS Thrombolytic Assessment System, Cardio Vascular Diagnostics Inc. pp. 1–4, Date Unknown.

Stat–Crit Hematocrit/Hemoglobin Measuring Instrument Instruction booklet, Wampole Laboratories, Cranbury, N.J., pp. 1–13, Date Unknown.

Thromboplastin–XS with Calcium, Sigma Diagnostics, pp. 1E–2E, Date Unknown.

Biotrack™512, Real–Time Measurement of Patient Coagulation Status: A Critical Need, CIBA–Corning, pp. 1–4, Feb. 1991.

DADE Innovin, DADE, LIMD1102, Rev. 2/96, pp. 1–2.

DADE Determination of INR (International Normalized Ratio), LIMD 1101–B, Rev. 3/96 p. 1.

Point–of–Care Coagulation Testing, The CoaguChek and CoaguChek Plus Systems, Boehringer Diagnostics, Boehringer Mannheim Corporation, Indianapolis, IN., pp. 1–8, 1995.

METHOD AND DEVICE FOR MEASURING BLOOD COAGULATION OR LYSIS BY VISCOSITY CHANGES

FIELD OF THE INVENTION

The present invention relates to a device and method for precisely measuring the coagulation or lysis of blood at the point-of-care. More particularly, a diagnostic device which is wholly or partly disposable is used to measure the viscosity change through the electrical conductivity of the blood or the diffusion coefficient or electrical conductivity of an electroactive species in the blood to perform a coagulation or lysis assay and display the assay results in real-time.

BACKGROUND OF THE INVENTION

The mechanism by which the body prevents loss of blood from the vascular system is known as hemostasis. Blood maintains a state of fluidity in normal circulation, but forms a barrier when trauma or pathologic conditions cause vessel damage. Coagulation tests measure the blood's ability to form a clot or coagulate and are used to manage a patient's anticoagulant therapy and diagnose hemostatic disorders. Lysis tests measure the reverse change where one is measuring the lytic activity of coagulated blood which is broken down to soluble degradation products by, for example, an enzyme plasmin.

There are two well-recognized coagulation pathways: the extrinsic or thromboplastin-controlled and the intrinsic or prothrombin/ fibrinogen-controlled coagulation pathway. Both the extrinsic and intrinsic pathways result in the production of thrombin, a proteolytic enzyme which catalyzes the conversion of fibrinogen to fibrin. Two routine coagulation tests measure the Prothrombin Time (PT) and the Activated Partial Thromboplastin Time (APTT). Both tests measure clotting time to evaluate a patient's baseline hemostatic state or to monitor the response to anticoagulant therapy as well as the overall function and status of the coagulant system.

The PT test is used to assess the extrinsic and common pathway clotting systems and for monitoring long term anticoagulant therapy. A common medication for long term anticoagulant therapy is sodium warfarin isopropanol clathrate, generally known by the brand name COUMADIN®, made by Dupont Pharmaceuticals of Wilmington, Del. Warfarin and its analogs induce anticoagulation by effectively blocking biosynthesis of Vitamin K dependent coagulation factors. Since the PT test measures clotting time, the effective amount of anticoagulant in the blood can be determined.

Another common medication which is in connection with cardiac bypass surgery, cardiac catheterization, renal dialysis, and in critical care situations for acute myocardial infarction is Heparin. The APTT test is widely used test for monitoring Heparin therapy for screening deficiencies of clotting factors included in the intrinsic and common coagulation system. Heparin exerts its anticoagulation effect by binding to and forming a complex with a plasma cofactor called antithrombin III.

Many laboratory clotting tests in the prior art are based on the phenomenon of measuring an endpoint which is a change of phase when a test sample changes from a liquid to a coagulated form. This phase change is due to the conversion of a soluble plasma protein fibrinogen to insoluble fibrin by the action of the enzyme thrombin. The clotting endpoint is physically detected by such secondary indicators as color or fluorescence detection by optical means and turbidity measurements through light scattering and magnetic particle oscillation. These laboratory instruments are relatively large because of the complex technology used, expensive, and designed for use by trained personnel due to the complexity of the detection methods. See generally U.S. Pat. No. 5,344,754. Large blood samples are also usually required.

Some prior art devices use porous membrane supports impregnated with layers of a reagent for enzymatic assays which rely on monitoring the intensity of the reaction product by optical spectroscopy such as reflectance, fluorescence, luminescence or color change. Such reagent impregnated membranes increase the complexity of the reaction's environment due to the absence of a liquid phase which is the ideal environment for reactions or phase transitions, and could further lead to possible interference with the enzymatic pathway. The accuracy of the results from membrane based systems are further affected by blood hematocrit and reaction volumes. The need for larger liquid samples of blood to achieve complete wetability of the membrane imposes yet another constraint. To overcome some of the problems with membranes, U.S. Pat. No. 5,418,141 teaches the use of expensive, high purity reagents. However, coagulation techniques which use Thrombin substrate chemistries suffer from a major drawback due to their insensitivity to fibrinogen deficiencies which could yield inaccurate clotting times.

Many studies of blood coagulation have attempted to demonstrate that measuring blood resistance detects clotting time and obtains a quantitative measurement of the rate of clot retraction. The results were usually not reproducible and there was "considerable variation and inconsistency in most methods in common use" as disclosed in Rosenthal, R. L., and Tobias C. W.: Measurement of the Electrical Resistance of Human Blood; Use in Coagulation Studies, J Lab Clin Med 33, 1110, 1948. Critical emphasis was placed upon the geometric orientation of the cell within which a pool of the blood sample was retained and the electrodes. It was also critical to prevent vibration of the cell. It was observed that as soon as the blood clotted, clot retraction begins by the contraction of the fibrin network which pulls the large elements or cells together into a dense mass, thus displacing the serum to the periphery. This process produces increases in resistance measurements because it simultaneously increases the concentration of poorly conducting cells and decreases the concentration of serum, a good conductor, between and around the electrodes. Prior to clot formation there is no significant change in resistance. The clotting time and start of clot retraction are marked by the first increase in resistance. Thus the clotting time may be determined only with the elimination of motion. Subsequent increases in resistance resulted from retraction of the clot. The slope of the rising portion of the time-resistance curve was assumed to correspond to the rate of clot retraction.

As later disclosed in Hirsch FG, et al: The Electrical Conductivity of Blood I. Relationship to Erythrocyte Concentration, Blood 5: 1017, 1950, "Some workers have attributed these changes to the effects of coagulation,[30–34] but others were unable to confirm these findings.[35,36] with certain designs of conductivity cells, blood resistance was observed to increase due to extrusion of serum during clot retraction,[32,35]. Blood conductivity was also found to vary with sedimentation,[35,37,38] agitation,[37] or stirring.[39–42]" It is further reported in Table I on page 1018 that the conductivity was unchanged during clotting and that only during clot retraction that there was a decrease in conductivity.

As disclosed in U.S. Pat. No. 4,947,678, a device measures viscosity changes in blood to determine blood coagulation. An electrically conductive sensor heats a blood sample by passing current through the sample. The temperature of the sensor is averaged using its surface temperature and the current applied to the sensor. The sample temperature is also monitored and the difference between it and the average sensor temperature is calculated. Changes in the calculated temperature difference is used as the indication of viscosity change.

Thus, a need exists in the field of diagnostics for a method and device for measurement of blood coagulation or lysis which is sufficiently inexpensive, timely, efficient, convenient, durable, and reliable for use in a diagnostic device which permits point-of-care use by untrained individuals in locations such as the home, sites of medical emergencies, or locations other than a clinic. Whether the device is disposable or reusable, there is also a need to operate with small blood sample sizes.

SUMMARY OF THE INVENTION

The present invention provides an electrode assembly which provides quantitative measurement of viscosity changes over intervals of time to signal the coagulation or lysis of a blood sample. The viscosity change is determined in real time by either the electrical conductivity of the blood or the diffusion coefficient or electrical conductivity of an electroactive species in the blood sample.

The present invention further provides a single-use electronic device for performing a coagulation or lysis assay of a blood sample. The device includes a housing having an exterior surface and defining an interior area and means for receiving the sample through the housing into the interior space. A non-porous substrate is positioned within the interior space for receiving the sample thereon. A reagent accelerates the coagulation of the sample and is positioned on the substrate and in contact with the sample. The device also includes means for measuring the viscosity of the sample and generating an electrical signal which correlates to a curve of the coagulation/lysis assay. Processing means positioned within the interior space is connected to the measuring means for receiving and converting the electrical signal into a digital output corresponding to the coagulation/lysis assay using assay calibration information stored therein. Display means visually displays the digital output external to the housing and is connected to the processing means.

A test card for the above electronic device is provided which generates a signal having a pre-determined frequency and determines a curve of a coagulation or lysis assay of a blood sample. The test card includes a non-porous substrate defining a surface for receiving the sample. A reagent is initially immobilized on the surface for contact with the sample. A plurality of electrodes are positioned on the substrate and contact the sample. The electrodes are adapted to receive and pass the signal into the sample. The electrodes generate an electrical signal corresponding to the viscosity of the sample which correlates to the curve of the coagulation/lysis assay.

A method of determining the coagulation or lysis of a sample is also provided by the present invention. The steps of the method include: introducing the sample to a sample receptor site on a substrate; accelerating the coagulation of the sample by chemically reacting the sample with at least one reagent on the substrate to produce a detectable change in the viscosity of the sample which correlates with the state of coagulation or lysis of the sample; measuring the viscosity of the sample and generating an electrical signal which correlates to a curve of the coagulation/lysis assay; and, processing the electrical signal into a digital output corresponding to the coagulation/lysis assay using assay calibration information.

The present invention also provides an electroactive species positioned on the substrate and in contact with the sample which enhances the sensitivity of measuring the electrolytic properties of the blood sample. Determining the electrolytic properties of the sample can include measuring the conductivity/resistivity or the diffusion coefficient of the electroactive species. Preferred electroactive species include ferricyanide, ferrocyanide, cadmium chloride, and methylviologen.

The present invention provides a coagulation measurement device which is sufficiently compact and inexpensive for use in a diagnostic device that is portable and disposable after a single use. The device also provides precise and accurate measurement of the reaction chemistry of the diagnostic device with results provided in a timely manner for the convenience of the user.

The advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

The present invention is preferably utilized in the disposable, single-use digital electronic instrument and assay devices. However, another preferred embodiment of the present invention uses a multiple-use or reusable device which is compact for hand-held operation or easy portability and is adapted to receive a disposal test card inserted therein. The present invention provides for the precise and accurate measurement of electrical or diffusion properties from one or more sampling areas located on one or more test cards to quantitatively perform a coagulation or blood lysis assay. The sampling areas can be one or more detection zones exhibiting a detectable change in the electrical or diffusion properties of the sample corresponding to the state of coagulation or lysis of the sample.

Figure 1:
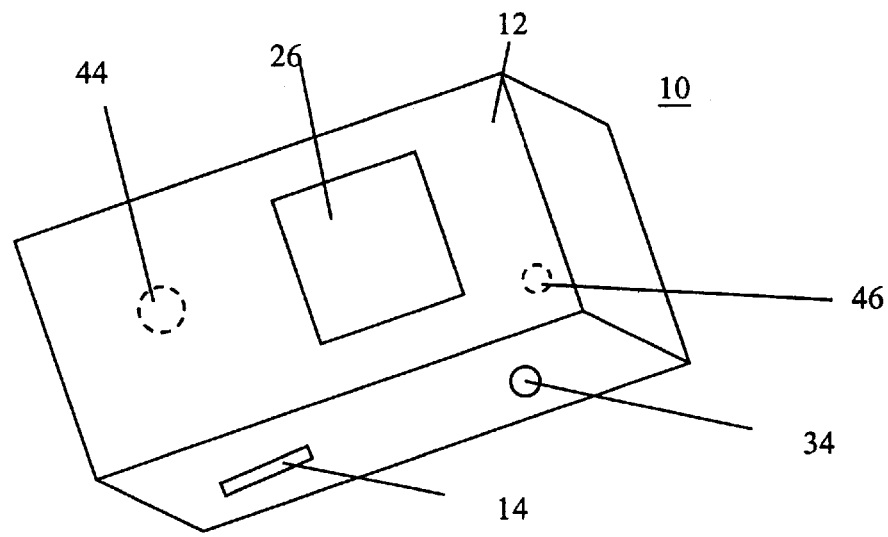
FIG. 1 is a perspective view of a diagnostic device of the present invention.
Figure 2:
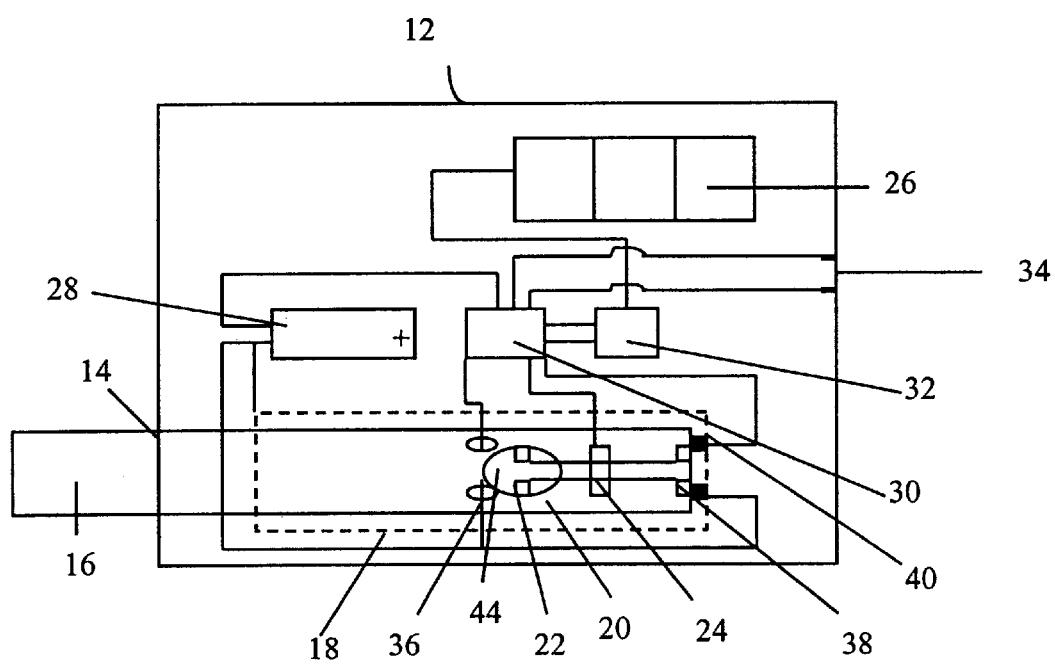
FIG. 2 is a schematic view of the diagnostic device illustrated in FIG. 1.

One embodiment of a reusable diagnostic device 10 of the present invention is illustrated in FIGS. 1 and 2. The device 10 includes a housing 12 having an inlet port 14 for receiving a test card 16 for at least partial insertion therethrough. The test card 16 is preferably disposal after performing the desired assay. The term test card 16 as used herein refers to any assay strip, cartridge, or other geometric shape which can support one or more reagents and electrodes as described herein. The device 10 itself may assume any convenient geometric shape as long as the electronics and chemistry described herein are cost effectively contained with acceptable performance.

FIG. 2 schematically illustrates a preferred embodiment of a circuit and the discrete electronics which control the measuring of electrical or diffusion properties of the sample during the coagulation or lysis assay. Mounted in the interior space of the housing 12 are all of the components, including a power supply 28 required to conduct the assay. Optionally, the device may provide a plug for an AC adaptor. The test card 16 inserts into the device and is positioned in thermal proximity to a heater 18 which is used to warm the sample on the test card to a pre-determined temperature above room temperature. Any conventional heater 18 of the appropriate size and heating capacity for the anticipated sample size is suitable. One example of a suitable heater 18 is manufactured by Minco which makes thermofoil heaters. The thermofoil heaters apply heat precisely and accurately directed to the test card 16 in the proximity of the sample without actually needing to touch the sample itself The thermofoil heaters contain thin and flexible heating elements sandwiched between a flexible insulation such as Kapton C. The element of the heater 18 is a flat foil instead of a tubular wire. Preferably, the thermofoil heater is mounted between or below a substrate such as aluminum or other thermally conductive material for efficient transfer of heat to the test card 16. Preferably, the temperature is maintained at 37° C. so that the test results can readily compared to other standardized test results without interpolation.

A temperature sensor 24 is mounted in proximity to the detection or sampling area 20 where the sample is applied or transported to in order to detect the temperature of the system and provide ambient temperature information for calibration adjustment at temperature extremes. It is suitable to locate the temperature sensor 24 anywhere in or on the device. For example, the temperature sensor 24 may be located on the test card 16.

The power supply 28 has a lead from its negative pole connected to one side of a electrode pair 22, and a lead from its positive pole being connected to an analog to digital converter 30 and display 26. A processor and memory component 32 is connected to the analog to digital converter 30 and the display 26. External ports 34 are connected to the analog to digital converter 30 for receiving assay calibration information, interfacing with a computer, or downloading test results. One end 38 of each of the electrode pair 22 electrically connects to a corresponding pair of contact pads 40 which provide connection to the processor 32 and the power source 28. The connection between the electrodes 22 and the contact pads 40 is made when the test card 16 is inserted into the inlet port 14.

The detection or sampling area 20 is configured to receive the sample directly or have the sample transported into the area. The detection area 20 includes one or more reagents which are initially immobilized on the surface of the test card 16 in the area. Upon application of the sample to the detection area 20, one or more of the reagents is wet by the sample and mixing therewith. The detection area 20 is also configured to retain the sample in contact with electrodes 22. The sample can also be treated by additional reagents or filtered before the sample is placed in contact with the electrodes 22.

Optionally, the test card 16 has an electrode pair 36 mounted thereon in proximity to the detection area 20, to detect the presence and movement of sample liquid on the test card 14. Presence of the sample liquid bridging the electrode pair 36 reduces the resistance across the electrodes, signaling the presence of a conductor (sample liquid) therebetween. When the sample contacts the electrodes 36 the chemical reactions are well underway and the instrument begins to read the reagent system. The reading may begin immediately when the sample contacts the electrodes 36 or there may be some time delay of about less than 1 second to 10 minutes (preferably from about 30 seconds to 2 minutes). There may be single or multiple readings or the readings may continue until the reagent system response has stabilized either to an endpoint, maximum or minimum, or to a constant reaction rate.

The processor 32 can be any common or custom integrated circuit with memory. The processor 32 must have the capacity to either store a set of pre-programmed calibration information or have the capability to be programmed during device manufacturing. In the case of preprogrammed calibration, selection of appropriate information during manufacture is necessary and can be done by laser burning of a selection of circuit pathways or any convenient means. In the case of post-manufacture calibration, a method to load calibration data onto the chip is necessary, for example external ports 34. External calibration can be accomplished with external electrical contacts or may be done with a non-contact method using radio waves, magnetic fields, pulse light, laser or the like. The non-contact method of calibration may be more practical and efficient from a manufacturing viewpoint.

The processor 32 will also control the entire operation of the instrument including, but not limited to, turning the instrument on in response to insertion of a test card 16, providing electrical power or time signals; timing with an on-board clock, recording, and processing the instrument zero function; controlling any time delays or timed steps during reading; determining when the assay has stabilized; receiving and processing information from the temperature sensor; and receiving input from measuring the electrical properties of the sample and converting it to output, based on calibration information, to the display. The processor will also determine if the coagulation or lysis reaction has occurred within the specified time, to a specified endpoint range or within a specified reaction rate range to control for inactive reagents. Any other electronic control checks can also be included. The processor 32 includes codes which identify the manufacturing lot numbers of the device components. The processor 32 contains a program which includes, but is not limited to, interpreting the current off the electrodes, relating the signal strength ratio to the reference strength, providing assay results, identifying potential errors, and performing other quality control checks.

Using these measurements with information stored in the processor 32 accurate results upon completion of each assay. Examples of the information stored in the microprocessor includes, but is not limited to, algorithms or calibration curves for the analytes selected for analysis and other assay calibration information; reaction stabilization, endpoint, or rate information; and manufacturing lot information on each of the chemical reagents, detectors, LEDs, assay strips, and other components used in the device.

The power supply 28 can be any convenient device including, but not limited to, a battery or a solar cell. The shelf life of the final product will be about 6 months to about 24 months at room temperature. The power supply must have stability consistent with this shelf life.

The display 26 preferably is a liquid crystal device LCD or any conventional, inexpensive display device. The number size in the display should be sufficiently large to allow most people to read the assay value, even if they have poor vision. The display height can be about 2.0 cm. The number of digits in the display can be anywhere from 1 to about 10 digits, however, a 3 to 5 digit display is usually sufficient. In addition to showing the assay result, the display may show messages relating to the assay result or processing or give error messages The converter 30 can include a multiplexer to integrate the signal from the electrodes and provide the digital signal to the processor 32. The processor can be used to count the time required for the integral to reach a fixed voltage comparator threshold. The time is proportional to the average signal over the sampling period.

In another preferred embodiment of the present invention, the entire device 10 can be disposable by having the test card 16 assembled as part of the device and sealed with all of the other components within the interior space of the housing during manufacturing. To introduce the blood sample onto the detection area 20 of the test card 16, a receptor port 44 seen in FIG. 1 extends from the surface of the housing 12 to its interior for receiving a sample. Once the sample is introduced through the receptor port 44, the sample is chemically reacted with at least one reagent 42 to produce a reaction product mixture corresponding to the state of coagulation or lysis of the sample. A portion of the reaction product mixture produces a detectable change in the electrical or diffusion properties of the sample which correlates with the coagulation or lysis state of the sample. Although the device 10 can be activated automatically by the insertion of the test card 16, a manual test button 46 can be optionally provided on the housing 12 to be externally accessible.

The device 10 can be of any convenient size with the optimal dimensions determined by several factors including convenience of use to the consumer. Preferably, the device 10 has a volume range of about 5 cm$^3$ to about 500 cm$^3$.

In the operation of one of the preferred embodiments of the present invention, the viscosity changes of a sample is determined by reacting the sample, within the housing of at least partially disposable device, with a reagent corresponding to assay for the sample to yield a detectable change in electrical or diffusion properties which correlates with the coagulation or lysis assay for the sample. Subsequently, the viscosity change is calibrated using the assay calibration information previously described and transformed to a numerical output. The assay calibration information is uniquely characteristic to the specific reagent in the housing and to the detectable change in electrical or diffusion properties for each sample.

The term specific reagent refers to the reagent contained in the individual device housing. For the single-use device which is entirely disposable, the chemistry (i.e. manufacturing lot number, etc.) of the specific reagent is known when the housing, interior components, and reagent are manufactured. As a result, the present invention can use assay calibration information that is unique to the specific reagent. Similarly, the assay calibration information can include specific, individual information on each component used in manufacturing the individual assay device. Preferably, the device is manufactured with the assay calibration information stored in the processor within the housing and all of the components sealed in the housing. For the single-use test card and reusable device, this information can be encoded on to the test card and read by the device upon insertion.

The assay calibration information can be used to determine the accuracy of the assay by measuring an electrical signal produced in response to the detectable change measuring viscosity through electrical or diffusion properties with a pre-determined range for the electrical signal. The detectable change can also be calibrated to a reference standard contained in or calculated using the assay calibration information. The assay results can also be adjusted to the ambient temperature of the device housing using the calibration information. The assay calibration information can be compared with the display output to determine the accuracy of the assay by including a pre-determined range for the display output in the information. Another method of determining the accuracy of the assay is to time the presence of the sample and compare the time required to achieve the assay result to the calibration information which can include a pre-determined range for that parameter.

Although one test card is analyzed by the embodiments illustrated above, the present invention also provides for sequentially analyzing multiple sampling areas on one test card or for analyzing more than two test cards either simultaneously or sequentially. Based upon the inventive concepts and embodiments described herein, it is within the scope of those skilled in the art to make the appropriate modifications.

Figure 3:
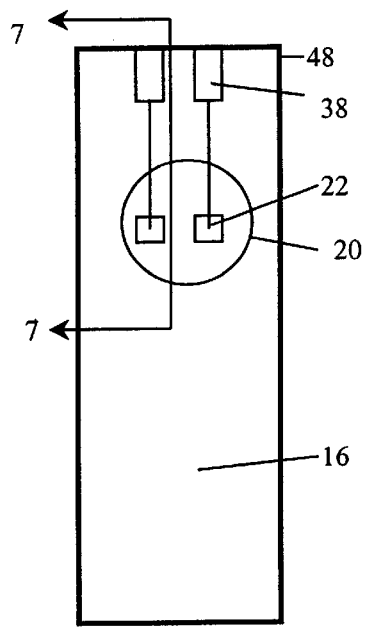
FIG. 3 is an embodiment of a disposable test card of the present invention for insertion into the device illustrated in FIG. 1 with an initially immobilized reagent and electrodes for measuring the viscosity changes of a blood sample.

The test card 16 of the present invention can have various configurations. FIG. 3 illustrates one embodiment wherein the electrode pair 22 is provided in the detection area 20. one end 38 of each of the electrode pair 22 electrically connects to a corresponding pair of contact pads 40 to provide connection to the processor 32 and the power source 28 as previously described in FIG. 2. The connection between the electrodes 22 and the contact pads 40 is made when the end 48 of the test card 16 is inserted into the inlet port 14.

Figure 4:
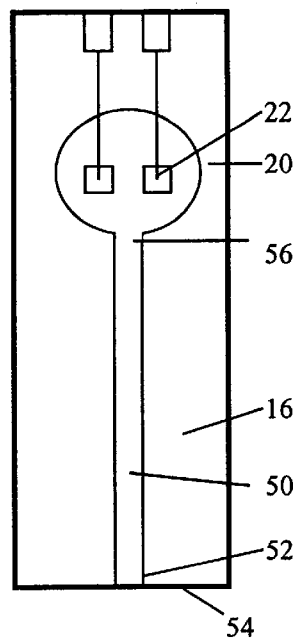
FIG. 4 is an embodiment of the test card as illustrated in FIG. 3 with a capillary channel for drawing a blood sample into contact with the electrodes.

FIG. 4 illustrates another embodiment of the test 16 wherein a capillary channel 50 is provided to transport a sample to the detection area 20. One end 52 of the capillary channel terminates in the proximity of the edge 54 of the test card which is not inserted into the inlet port 14. The opposite end 56 of the capillary channel connects to the detection area 20.

Figure 5:
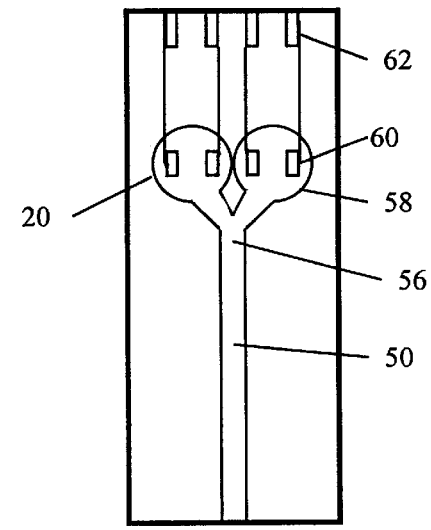
FIG. 5 is an embodiment of the test card of the present invention having two sets of electrodes in distinct testing areas for performing a separate on-board control test.

FIG. 5 shows another embodiment of a test card 16 which provides an on-board control test area 58 having a pair of electrodes 60 for contacting the sample. One end 62 of each of the electrode pair 60 electrically connects to a corresponding pair of contact pads 40 to provide connection to the processor 32 and the power source 28 as previously described in FIG. 2. The capillary 50 bifurcates at end 56 to transport the sample to both the detection area 20 and the control test area 58. Having a control test area 58 separate from the detection area 20 allows the immobilization of different reagents in the control test area than in the detection area.

Figure 7:
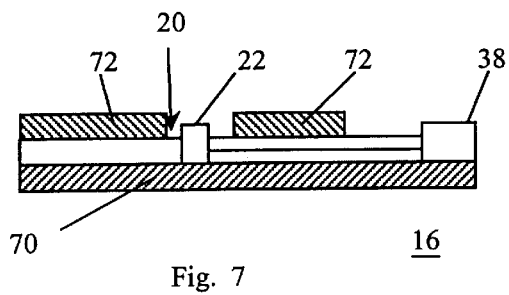
FIG. 7 is a cross-sectional view of a test card of the present invention.

FIG. 7 is a cross-sectional view of the test card 16 which uses a non-porous substrate 70 preferably made of a polymeric material. A top sheet 72, also made of a non-porous material, is placed over the substrate 70 defining the detection area 20. The electrode 22 is located in the detection area 20 and extends to the end 38.

The present invention also provides a reagent system for use in coagulation or lysis assays that rely on the generation of an electrical signal (voltage, current, etc.) indicative of the blood clotting or lysis process. These reagent compositions are particularly useful in assay devices in which a liquid blood or plasma specimen is transported by capillary action into the test card which contains the reagent and in which the assay is performed.

The reagent compositions have been developed primarily for use in blood coagulation or blood lysis assays which rely on changes in the viscosity and ultimately the reduction or increase in ionic mobility and or diffusion characteristics of an added electroactroactive species of the blood or plasma sample as measured by the generation of an electrical signal (current or voltage). Blood is an electrolyte and can therefore conduct or carry an electric current. Electrolytic conductance is a measure of the ability of a solution of electrolytes to carry an electrical current by virtue of the mobility of its ions under the influence of a potential gradient. The ionic mobility and diffusion kinetics is a function of the solution viscosity, ionic size and charge and the magnitude of the applied potential. When blood begins to clot or coagulate, it thickens or causes its viscosity to increase. This increase in viscosity inhibits or retards the ionic mobility. The retardation of ionic mobility is directly proportional to a reduction in the electrical current of the total solution. During the clotting process, the blood clot retracts and the fibrin monomers come together to form a clot. Addition of the electroactive chemical species to the reagent composition enhances the conductivity of unclotted blood by modulating the measured signal. This enhancement leads to increased sensitivity and reliability of the detection technique. As clotting occurs, the fibrin clot retards the movement of ions and consequently the current reduces. Until such time when the clotting is complete, there may be a slight increase in the current of the clot due to aggregation of the electroactive species in spite of restricted ionic mobility and or diffusion. Such a current time profile is extremely useful in determining the onset of clotting as well as the endpoint of the clotting process and could conceptually provide a very accurate means of determining blood clotting times in PT, APTT and other clotting assays. The sensitivity of these type of current or voltage time measurements is inherent in the direct measurement technique and does not rely on secondary or indirect indicators such as color or fluorescence detection by optical means and turbidity measurements by light scattering methods. Simultaneously the effect of thrombolytic therapy on blood clots, using for example Tissue Plasminogen Activator, the time taken to solubilize the clot (also referred to as the Clot Lysis Time or Lysis Onset Time) can also be determined by this method. If it is assumed that the baseline current of the clot is high due to presence of aggregated electroactive species than as the clot dissolves there will be initially a reduction in current followed by a sharp increase due to increased ionic mobility or diffusion characteristics.

For PT assays the reagent matrix normally consists of thromboplastin purified from an aqueous extract of acetone dried brain tissue, which contains many components and impurities. In contrast, synthetic recombinant thromboplastin (r-DNA thromboplasin) consists of a relatively well defined complex form by purified recombinant tissue factor protein and a purified artificial lipid component. The present invention provides a reagent composition including either thromboplastin purified and isolated from brain tissue or r-DNA thromboplastin capable of providing a PT result independent of any adverse factors.

The reagent compositions are preferably aqueous solution which can be applied to the test card using various types of micro-dispensing techniques which include, but is not limited to, ink jet, striper, and sprayer deposition methods, or dip coating and air dried in situ during the manufacturing process. In one such solution, thromboplastin reagent and electroactive speciess used in coagulation assays are mixed in a homogeneous aqueous solution containing an appropriate proportions of spontaneously hydratable and soluble carbohydrate chemical species such as sucrose, starch, dextrose, dextran, maltodextrin, other water soluble polymers, binding agents and the like. The use of the carbohydrate species is to facilitate hydration and stabilize the reagent matrix during the solvation with the liquid sample such as blood or plasma.

The present invention also provides for detecting or measuring the changes in the diffusion constant or kinetic profile of an electroactive species which is added to the blood sample as a function of time while the fluid undergoes clotting. Any electrochemical technique that allows the determination of the diffusion kinetics/constants of an electroactive substance is suitable for use with the present invention. A known concentration of an electroactive species is dissolved in the sample and an apparent diffusion coefficient can then be measured. The information obtained depends on the nature of the electroactive species. Suitable electrochemical techniques include polarography, cyclic voltammetry (CV), rotating disk voltammetry (RDV), chronoamperometry/chronocoulometry, and chronopotentiometry and are disclosed by E. Dayalan et al., "Micelle and Microemulsion Diffusion Coefficients", *Electrochemistry in Colloids and Dispersion*, VCH Publishers, Inc. New York 1992 and the references cited therein, which is hereby incorporated in its entirely by reference. The current-diffusion coefficient relationships that are applicable for each of these techniques are as follows:

Polarography (Ilkovic equation)

$$i_d = 708 n C D^{1/2} m^{2/3} t^{1/6}$$

Cyclic voltammetry (Randles-Sevcik equation)

$$i_p = 0.4463 (n^{3/2} F^{3/2})/(R^{1/2} T^{1/2}) \, ACD^{1/2} v^{1/2}$$

Rotating disk voltammetry (Levich equation)

$$i_f = 0.62 n F A C D^{2/3} v^{-1/6} W^{1/2}$$

Chronoamperometry (Cottrell equation)

$$i(t) = n F A C D^{1/2} \pi^{-1/2} t^{-1/2}$$

Chronopotentiometry (Sand equation)

$$i(\tau) = 1/2 n F A C D^{1/2} \pi^{-1/2} \tau^{-1/2}$$

The symbols in the above mean the following: $i_d$ is the polarographic diffusion-limited current (A), n is the number of electrons transferred, C is the concentration of the electroactive probe (mol cm$^{-3}$), D is the diffusion coefficient of the electroactive probe (cm$^2$ s$^{-1}$), m is the mass flow rate of mercury at the dropping electrode (mg s$^{-1}$), t is the drop time (s), $i_p$ is the peak current (A), F is Faraday's constant (coulombs mol$^{-1}$), A is the area of the electrode (cm$^2$), R is the gas constant (J mol$^{-1}$), T is the temperature (K), v is voltage scan rate (V s$^{-1}$), $i_l$ is the limiting current (A), v is the kinematic viscosity of the solution (cm$^2$ s$^{-1}$), w is the angular velocity of the rotating disk electrode (rad s$^{-1}$), i(t) is the diffusion current (A) at time t(s), and τ is the transition time (s).

Preferred electrochemical methods are voltammetry, cyclic voltammetry, chronoamperometry, and chronopotentiometry. In these methods the current measured is proportional to the diffusion coefficient of the electroactive species which is related to the viscosity of the sample measured over time. Generally, in chronoamperometry, the potential or voltage is applied at a constant level, for example 400 millivolts or another suitable voltage, which is sufficient to oxidize or reduce the electroactive species which will result in a change of current over time. In cyclic voltammetry the voltage is cycled at two different potentials. In chronopotentiometry the current is applied in a constant or prescribed change manner and the potential is measured over time.

Figure 6:
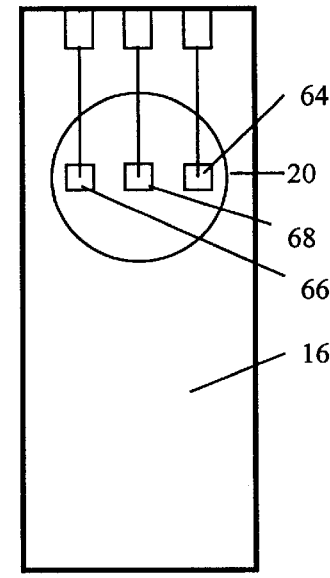
FIG. 6 is another embodiment of a test card of the present invention having a working electrode, a counter electrode and a reference electrode.

A voltammetric method applies a potential and measures the current as a function of time. Two variations of this method keeps the applied potential constant or changes the potential in a prescribed manner. Preferably, a voltammetric method is used to measure the diffusion limited current of the electroactive species. The device measures the diffusion limited current of the electroactive species present in the reagent. The diffusion limited current is related to the diffusion coefficient of the electroactive species in the sample which is directly a measurement of the viscosity change of the sample. FIG. 6 illustrates a disposable test card 16 which provides a miniaturized electrochemical cell including a working electrode 64, a reference electrode 66 and preferably a counter electrode 68 in the detection area 20. The electrodes can be made from different types of metal. Preferably, the working electrode 64 and counter electrodes 68 are made of graphite/carbon, gold or platinum and the reference electrode 66 is made of silver/silver chloride.

Preferred electroactive species are water soluble and form a redox couple. More specifically, ferricyanide, ferrocyanide, cadmium chloride, and methylviologen are most preferred electroactive species for use with the present invention.

The reagent compositions immobilized on the inventive test cards have been developed primarily for use in blood coagulation or blood lysis assays which rely on changes in the viscosity and ultimately the reduction or increase in ionic mobility or changes in the diffusion kinetics of the blood plasma sample as measured by the generation of an electrical signal (current or voltage). Since blood is an electrolyte and can therefore conduct or carry an electric current. Electrolytic conductance is a measure of the ability of a solution of electrolytes to carry an electrical current by virtue of the mobility of its ions under the influence of a potential gradient. The ionic mobility and diffusion kinetics is a function of the solution viscosity, ionic size and charge and the magnitude of the applied potential. When blood begins to clot or coagulate, it thickens or causes its viscosity to increase. This increase in viscosity inhibits or retards the ionic mobility. The retardation of ionic mobility is directly proportional to a reduction in the electrical current of the total solution. During the clotting process, the blood clot retracts and the fibrin monomers come together to form a clot. As clotting occurs, the fibrin clot retards the movement of ions and consequently one can expect a reduction in the current. Such current time profile is extremely useful in determining the onset of clotting as well as the endpoint of the clotting process and could conceptually provide a very accurate means of determining blood clotting times in PT, APTT and other clotting assays. The sensitivity of these type of current or voltage time measurements is inherent in the direct measurement technique and does not rely on secondary or indirect indicators. To enhance the stability of the reagents on the test card, it is preferred to add a preservative such as thimerosol, a surfactant such as triton and additional buffer salts.

The present invention can also be applied to a skin bleeding time procedure in which blood issuing from a standardized wound is progressively quantitated by the increasing conductivity between a surface electrode and underlying skin. The test card described herein can be placed directly on the wound of a patient. If necessary, the formation of a standardized wound can be made by incorporating an appropriately shaped lancet as part of the test card. The blood emanating from the wound can be directly applied to the surface of the test card.

Having generally described the present invention, a further understanding can be obtained by reference to the following specific examples, which are provided herein for purposes of illustration only and are not intended to be limiting of the present invention.

EXAMPLES

Unless otherwise indicated, the following tests used a commercially available reagent thromboplastin-XS with calcium (Pt) which was obtained from Dade International of Miami Fla. and sold under the tradename INNOVIN® which is a dried recombinant human tissue factor with calcium. The Pt reagent accelerates the clot formation rate usually forming a clot in about 45 seconds. The Pt reagent contains a source of tissue thromboplastin and was reconstituted with deionized water as required by the manufacturer, dispensed on a microelectrode, and partially air dryed. No additional additives like a preservative or surfactant was used. The microelectrode was fabricated by Applied Graphics of Soquel, Calif. by printing a thin layer of silver to form the electrodes onto the surface of a non-porous test card in the configuration illustrated in FIG. 3. The test card was washed with water and alcohol prior to use. All tests were carried out at ambient temperature. Once the blood sample was applied to the microelectrode containing the Pt reagent, the clotting profile was manually recorded using a conventional conductivity meter connected to the contact pads of the electrodes. The meter is manufactured by Horiba in Japan.

Figure 8:
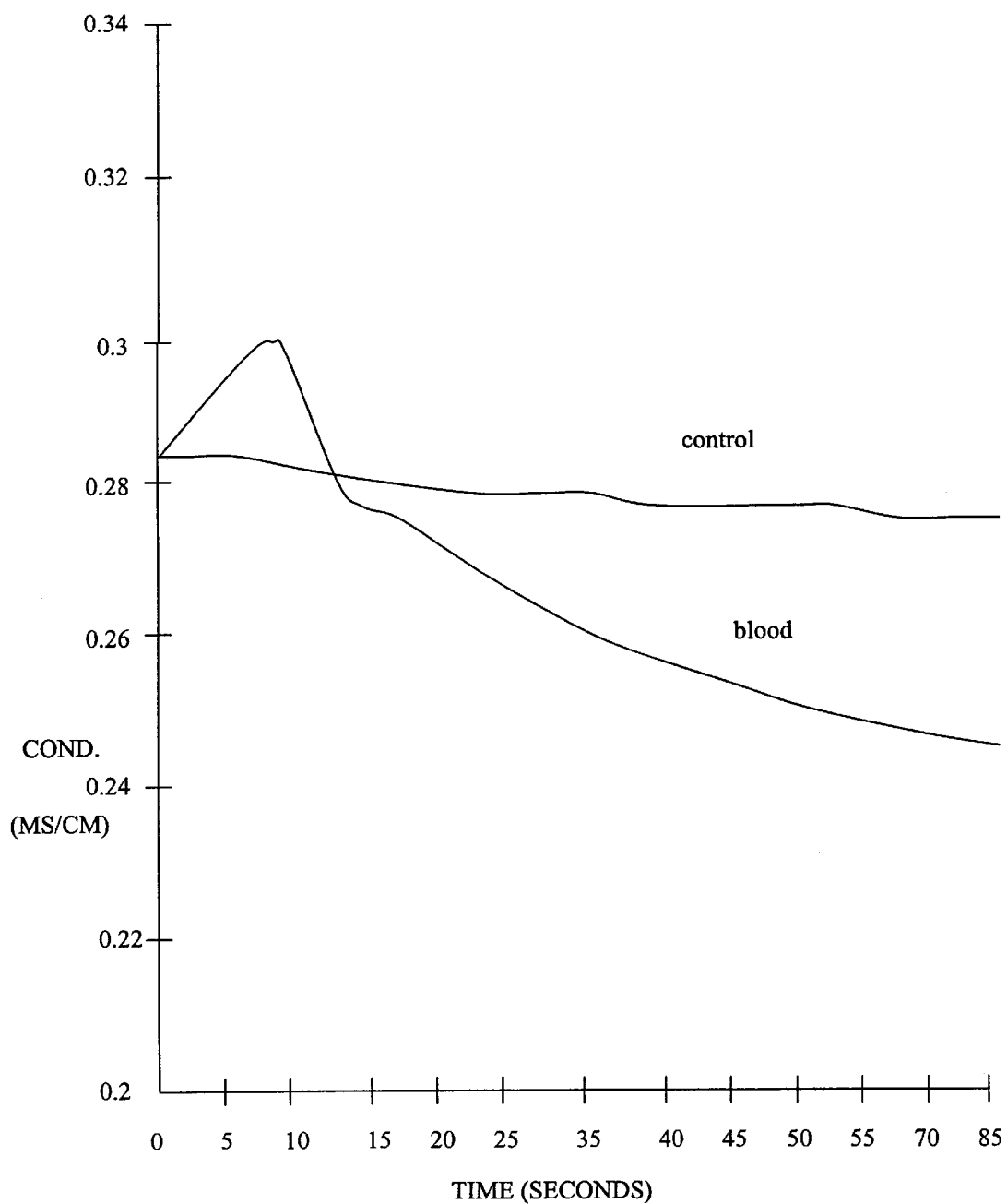
FIG. 8 is graph of conductivity in mS/cm vs. Time in seconds which illustrates a change in conductivity with increasing viscosity as a whole blood sample coagulates.
Figure 9:
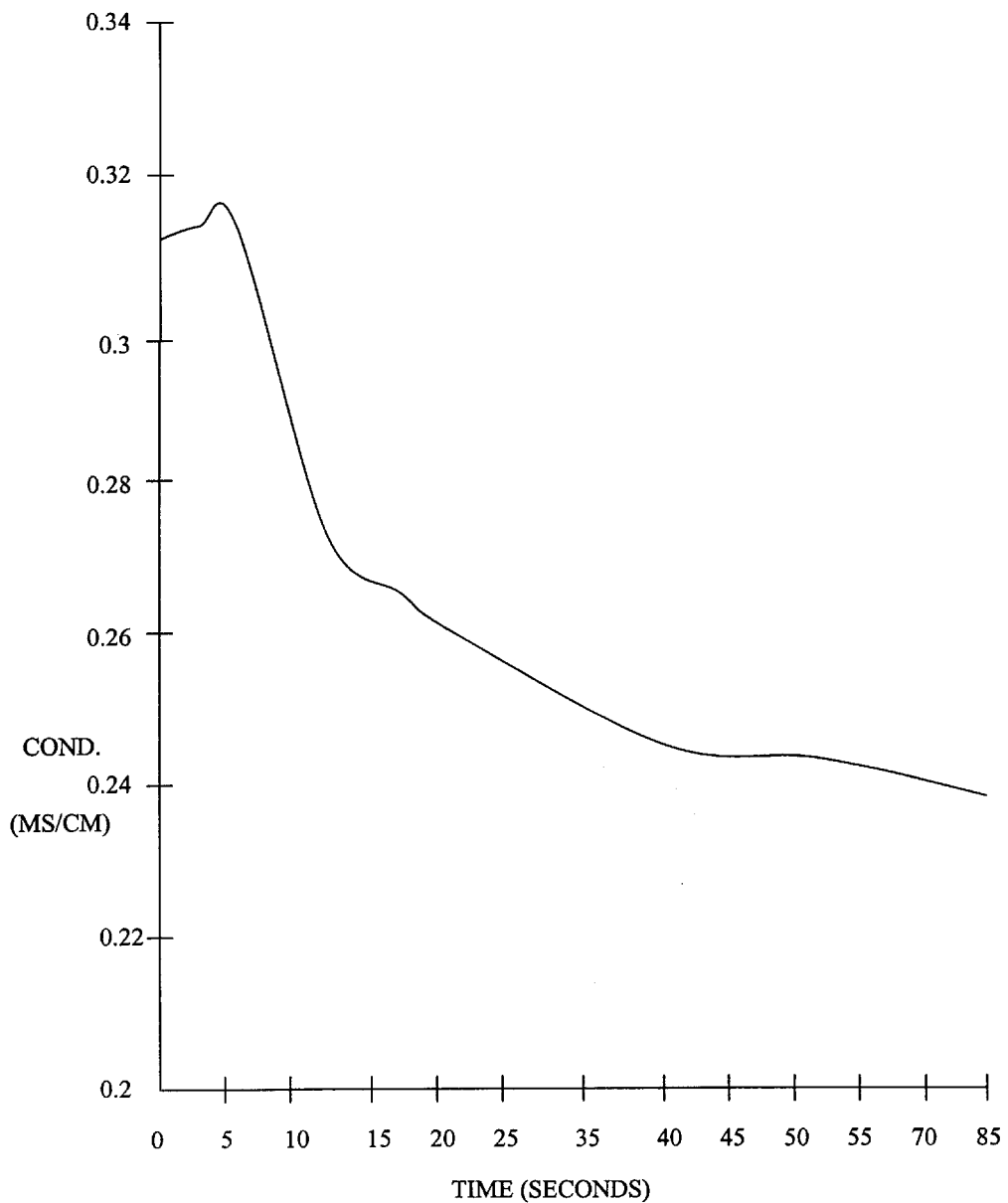
FIG. 9 is a graph of conductivity in mS/cm vs. time in seconds which illustrates the change in conductivity during the test.

FIG. 8 illustrates a change in conductivity with increasing viscosity as a whole blood sample coagulates. FIG. 9 plots the change in conductivity during the test. The conductivity was measured immediately upon drawing until the sample began to coagulate. The conductivity starts at about 0.31 mS/cm and, as discovered herein, characteristically decreases somewhat uniformly until the conductivity levels off at about 0.24 mS/cm at which point the conductivity begins to rise. It was observed that removal of the clogging left only serum which is primarily electrolyte and affected the increase in conductivity.

Clotting Time is determined by plotting the conductivity decrease between t=0 and about t=150 seconds from these test results and surprisingly yields an accurate Clotting Time measurement which can be correlated to the PT Time. Although the tests were not optimized and did not use a temperature control, the conductivity changes during the blood/plasma coagulation process are clearly demonstrated.

Other tests were run as a control with Pt reagent and salt water to check that the characteristic curve was the result of coagulation. The resulting curves were flat which indicated that the response seen in FIG. 8 was indeed the result of coagulation. Over the same period of time, the viscosity of tap water will not change and remains fairly constant.

Figure 10:
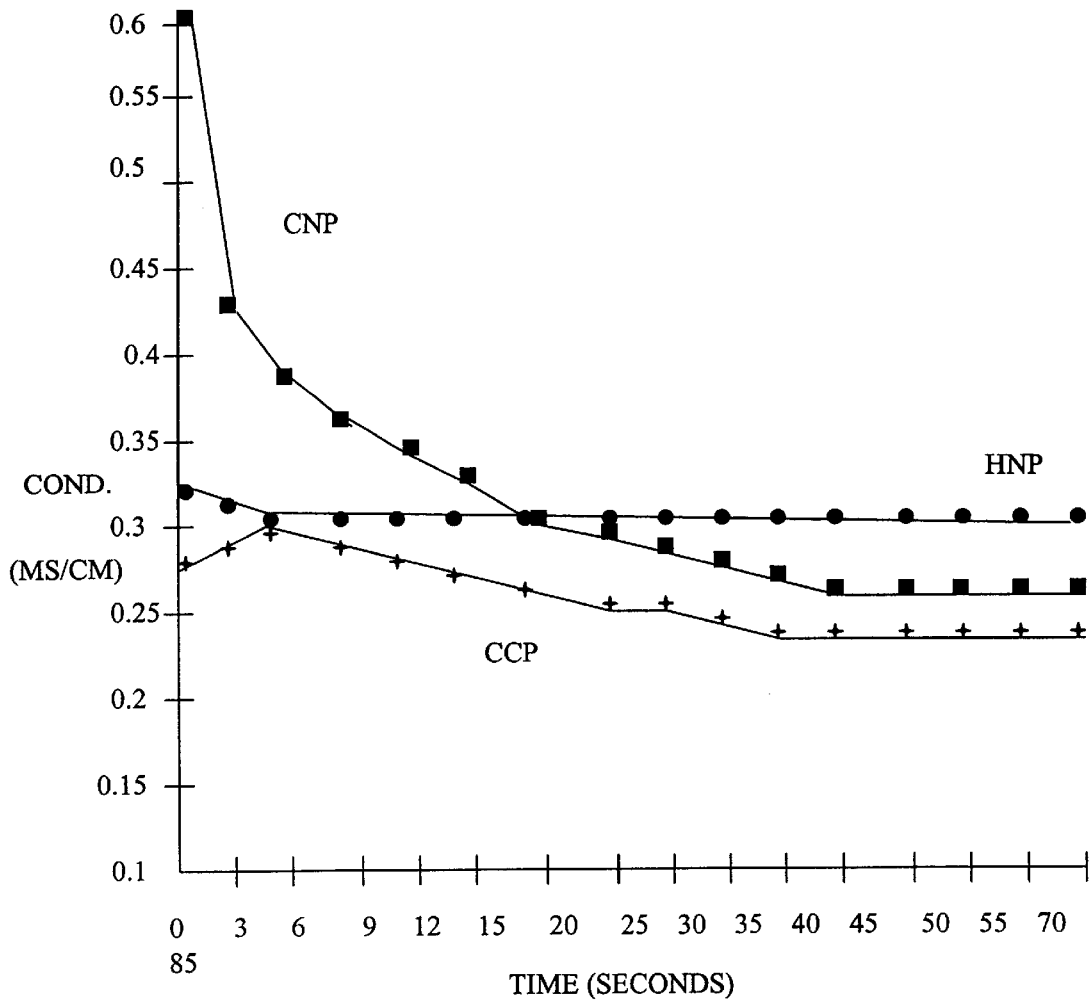
FIG. 10 compares a normal plasma sample which has been citrated (CNP) with a heparinised normal plasma sample (HNP) and a citrated COUMADIN plasma sample (CCP) in a graph of conductivity vs. time.

FIG. 10 compares a normal plasma sample which has been citrated (CNP) with a heparinised normal plasma sample (HNP) and a citrated COUMADIN plasma sample (CCP). The graph demonstrates that the CNP curve exhibited the fastest clotting. The CCP curve of a patient undergoing anticoagulant therapy with COUMADIN exhibits the characteristic slope illustrated above, but clearly differs from the normal plasma sample. The HNP curve of a patient treated with Heparin exhibits a more extreme response to an anticoagulant drug.

Figure 11:
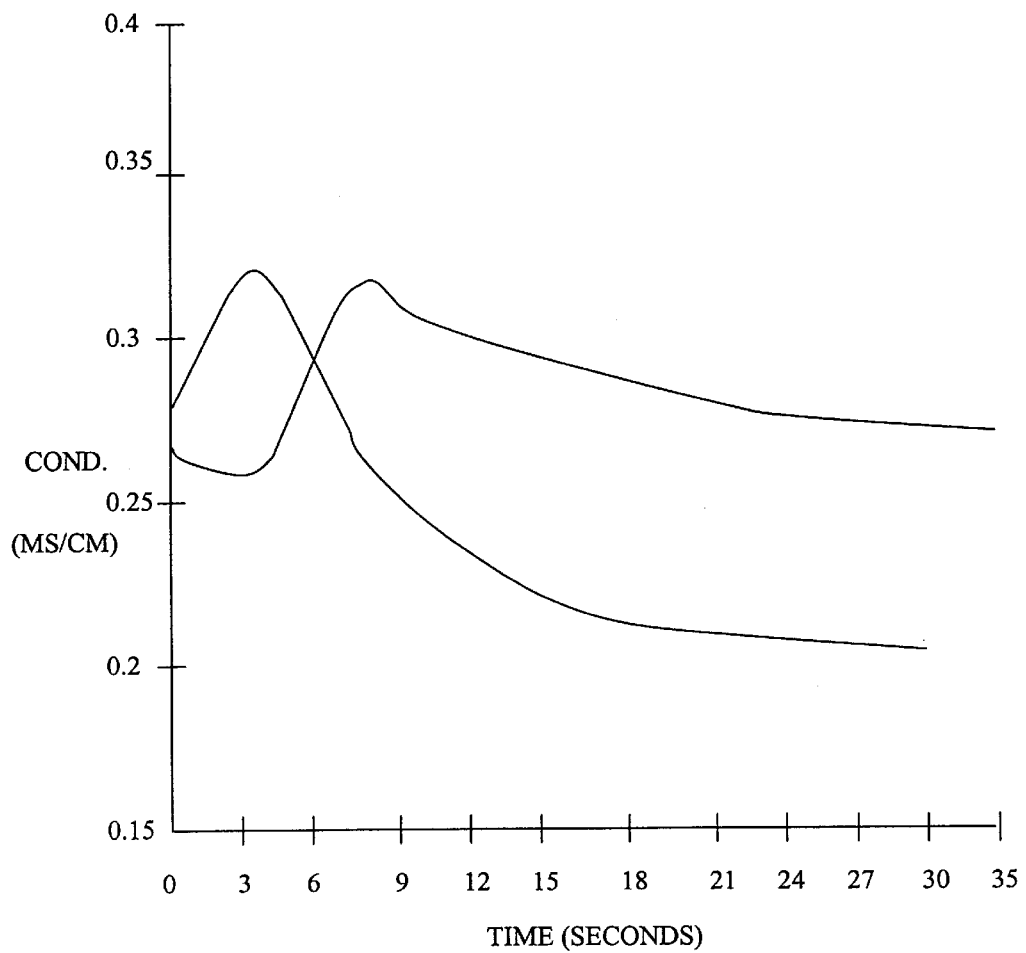
FIG. 11 illustrates the clotting profiles of whole blood samples comparing a Heparinized sample and a citrated sample in a graph of conductivity vs. time.

FIG. 11 illustrates the clotting profiles of whole blood samples comparing a Heparinized sample and a citrated sample. Again, the characteristic effect is present even in the whole blood of a patient being treated with Heparin. Several sets of these tests were run to confirm reproducibility.

The present invention is useful in many types of coagulation and lysis assays. For example, and not for limitation, applications of the present invention include PT, APTT, thrombin time, fibrinogen assays, and platelet detection. For fibrinolytis assays a lytic agent such as a tissue plasminogen activator will be incorporated in the clotting reagent mixture. After clotting occurs there is an increase in conductivity indicating the onset of lysis.

Numerous modifications and variations of the present invention are possible in light of the above teachings. It is therefore to be understood that within the scope of the appended claims, the invention may be practiced otherwise than as specifically described herein.

What is claimed is:

1. A single-use electronic device for performing a coagulation or lysis assay of a blood sample, the device comprising:
    a housing having an exterior surface and defining an interior area;
    means for receiving the blood sample through the housing into the interior area;
    a non-porous substrate positioned within the interior area for receiving the blood sample thereon;
    a reagent for accelerating the coagulation of the blood sample positioned on the substrate and in contact with the blood sample;
    an electroactive species positioned on the substrate and in contact with the blood sample;
    means for measuring the viscosity of the blood sample and generating an electrical signal which correlates to a curve of a coagulation or lysis assay;
    processing means being positioned within the interior area and connected to the measuring means for receiving and converting the electrical signal into a digital output corresponding to the coagulation or lysis assay using assay calibration information stored in the processing means; and
    display means for visually displaying the digital output external to the housing, the display means being connected to the processing means.

2. The device of claim 1 wherein the measuring means includes:
    means for generating a signal of predetermined frequency, the generating means being positioned within the interior area;
    a plurality of electrodes being positioned on the substrate and contacting the blood sample, the electrodes connecting to the generating means for passing the signal into the blood sample, the electrodes generating an electrical signal corresponding to the conductivity/resistivity of the blood sample.

3. The device of claim 1 wherein the measuring means includes:
    means for generating a signal of predetermined frequency, the generating means being positioned within the interior area;
    a plurality of electrodes being positioned on the substrate and contacting the blood sample, the electrodes connecting to the generating means for passing the signal into the blood sample, the electrodes generating an electrical signal corresponding to the diffusion coefficient of the electroactive species.

4. The device of claim 1 wherein the electroactive species is selected from the group consisting of ferricyanide, ferrocyanide, cadmium chloride, and methylviologen.

5. The device of claim 1 wherein the device further includes a heater being positioned within the interior area and in thermal contact with the substrate so that the substrate can be warmed to a pre-determined temperature upon receiving the blood sample.

6. The device of claim 1 wherein the processing means further calibrates the electrical signal to a reference standard using the stored assay calibration information.

7. The device of claim 1 wherein the processing means further receives the ambient temperature of the assay device from a sensor within the housing and adjusts assay results using the stored assay calibration information.

8. The device of claim 1 wherein the assay calibration information stored in the processing means determines results for at least one of assays selected from the group consisting of a Prothrombin Time, an Activated Partial Thromboplastin Time, platelet aggregation, and fibrinogen.

9. A test card for an electronic device which generates a signal having a pre-determined frequency and determines a curve of a coagulation or lysis assay of a blood sample, the test card comprising:
    a non-porous substrate defining a surface for receiving the blood sample;
    an electroactive species positioned on the substrate and in contact with the blood sample;
    a reagent initially immobilized on the surface for contact with the blood sample; and
    a plurality of electrodes being positioned on the substrate and contacting the blood sample, the electrodes adapted to receive and pass the signal into the blood sample, the electrodes generating an electrical signal corresponding to the viscosity of the blood sample which correlates to the curve of the coagulation or lysis assay.

10. The test card of claim 9 wherein the electrical signal generated by the electrodes measures the conductivity/resistivity of the blood sample.

11. The test card of claim 9 wherein the electrical signal generated by the electrodes measures the diffusion coefficient of the electroactive species.

12. The test card of claim 9 wherein the electroactive species is selected from the group consisting of ferricyanide, ferrocyanide, cadmium chloride, and methylviologen.

13. A method of determining the coagulation or lysis of a blood sample, the steps of the method comprising:

introducing the blood sample to a sample receptor site on a substrate and contacting an electroactive species positioned on the substrate with the blood sample;

accelerating coagulation of the blood sample by chemically reacting the blood sample with at least one reagent on the substrate to produce a detectable change in the viscosity of the blood sample which correlates with a state of coagulation or lysis of the blood sample;

measuring the viscosity of the blood sample and generating an electrical signal which correlates to a curve of a coagulation or lysis assay; and processing the electrical signal into a digital output corresponding to the coagulation or lysis assay using assay calibration information.

14. The method of claim 13 wherein the method includes the step of displaying the digital output.

15. The method of claim 13 wherein the measuring step includes:

generating a signal of predetermined frequency;

contacting a plurality of electrodes with the blood sample;

passing the signal of predetermined frequency through the electrodes into the blood sample; and generating the electrical signal with the electrodes corresponding to the conductivity/resistivity of the blood sample.

16. The method of claim 13 wherein the measuring step includes:

generating a signal of predetermined frequency;

contacting a plurality of electrodes with the blood sample;

passing the signal of predetermined frequency through the electrodes into the blood sample; and generating the electrical signal with the electrodes corresponding to the diffusion coefficient of the electroactive species.

17. The method of claim 13 wherein the method includes calibrating the electrical signal to a reference standard using the assay calibration information to determine results for at least one of assays selected from the group consisting of a Prothrombin Time, an Activated Partial Thromboplastin Time, platelet aggregation, and fibrinogen.

* * * * *